United States Patent [19]

Zhagars et al.

[11] Patent Number: 4,718,994

[45] Date of Patent: Jan. 12, 1988

[54] METHOD FOR PREPARING HYDROXY COMPOUNDS OF AROMATIC AND HETEROAROMATIC SERIES

[75] Inventors: Andrei K. Zhagars; Voldemar Y. Grinshtein, both of Riga; Sniedzite A. Ozola, Rizhsky raion; Andris K. Zitsmanis; Avgust K. Arens, both of Riga, all of U.S.S.R.

[73] Assignee: Latviisky Gosudarstvenny Universaitet Imeni P. Stuchki, Riga, U.S.S.R.

[21] Appl. No.: 745,267

[22] Filed: Jun. 14, 1985

[51] Int. Cl.⁴ .............................................. C25B 3/00
[52] U.S. Cl. .................................. 204/73 R; 204/72; 204/74; 204/75; 548/496; 548/497; 548/498; 562/774; 562/444; 562/451; 568/771
[58] Field of Search ..................... 204/72, 73 R, 73 A, 204/74, 75; 548/496–498; 562/774, 444; 568/771

[56] References Cited

U.S. PATENT DOCUMENTS 4,137,404  1/1979  Batcho et al. ...................... 548/497

OTHER PUBLICATIONS

The Enzymes Ed., P. O. Bayuer, vol. XII Third Edition, Acedemic Bess N.J., San Francisco, London (1975) pp. 211–226.
J. Heterocycl. Chemistry, 1979, 16, pp. 1325–1328 by Kunio Saito, et al.
J. Am. Chem. Soc., 1982, 104, pp. 1666–1671 by Helen W. Richter, et al.
J. Am. Chem. Soc., 1983, 105, No. 16, pp. 5434–5440 by Helen W. Richter, et al.

Primary Examiner—R. L. Andrews
Attorney, Agent, or Firm—Burgess, Ryan & Wayne

[57] ABSTRACT

A method for perparing hydroxy compounds of the aromatic and heteroaromatic series of the general formula:

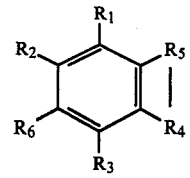

wherein when $R_1=-COOH$, $-CH_2CH(NH_2)COOH$ then $R_2=-OH$, $-H$, $-COOH$; $R_3=-H$, $-OH$; $R_4$, $R_5=-H$ with no connecting bond; $R_6=-OH$; and when $R_1,R_6,R_3=-H$, $R_2=-OH$; then $R_4=>NH$; $R_5=-CR_7=CHR_4$, where $R_7=-CH_2-CH_2-NH_2$, $-CH_2-CH(NH_2)COOH$, consists in that aromatic and heteroaromatic compounds of the general formula

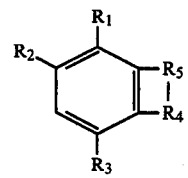

wherein when $R_1=-COOH$, $-CH_2CH(NH_2)COOH$, then $R_2=-OH$, $-H$, $-COOH$; $R_3=-H$, $-OH$; $R_4,R_5=-H$ with no connecting bond; and when $R_1,R_2,R_3=-H$, then $R_4=>NH$; $R_5=-CR_7=CHR_4$, where $R_7=-CH_2-CH_2-NH_2$, $-CH_2-CH(NH_2)COOH$. are subjected to hydroxylation in the presence of oxygen, phenazine catalysts of the general formula

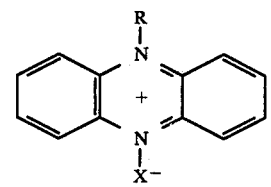

wherein R is $CH_3$,

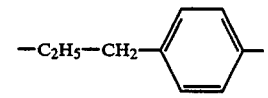

styrenedivinylbenzene copolymer $X^-=CH_3SO_4^-$, $C_2H_5SO_4^-$, $Cl^-$, and a reducing agent performing one-electron reduction of the heterocyclic nitrogen of the phenazinium cycle at a pH of the reaction medium ranging from 2.0 to 5.5, followed by isolation of the desired product.

6 Claims, No Drawings

METHOD FOR PREPARING HYDROXY COMPOUNDS OF AROMATIC AND HETEROAROMATIC SERIES

FIELD OF APPLICATION

The present invention relates to organic chemistry and chemistry of naturally-occurring compounds; more particularly it relates to a method for preparing hydroxy compounds of the aromatic and heteroaromatic series useful in medicine and in the synthesis of a number of pharmaceutical preparations.

Known in the art is an enzymatic process for preparing hydroxy compounds of the aromatic and heteroaromatic series based on the use of enzymes of monohydroxygenase by way of enzymatic hydroxylation of the aromatic ring. For the hydroxylation such enzymes as salicylatehydroxylase, tyrosinehydroxylase, n-hydroxybenzoate hydroxylase, tryptophan-5 monohydroxygenase are employed.

The starting products are intermixed under sterile conditions with monohydroxygenase and the hydroxylation process is conducted in the presence of a reductase, tetrahydropteridine and a reduced phosphate of nicotine-amide-adenine-dinucleotide at a predetermined temperature and pH of the reaction medium, followed by isolation of the desired product (cf. The Enzymes, Ed. P. O. Bayeur, vol. XII, 3-rd Edition, Academic Press, N.Y.-San Francisco-London, 1975, p. 647).

However, these methods have not found any commercial implementation due to difficulties associated with the industrial-scale production, complicated operations of purification of enzymes and instability of the latter under the conditions of the reaction of hydroxylation.

Also known in the art are methods for preparing hydroxy compounds of the aromatic and heteroaromatic series from naturally-occurring products; for example, serotonin is prepared from bovine serum, bananas or *Hoppophae Rhamnoides* (sea buckthorn) bark, or, for example, 3,4-dihydroxyphenylalanine is produced from bone and brain liquid of guinea pigs and rabbits (cf. S. Kunic, J. Heterocyclic Chem., 1979, /16/7/, p. 1325-1328).

Also known are synthetic methods for the preparation of hydroxy compounds of the aromatic and heteroaromatic series for example, a method for preparing serotonin and tryptamine. The process is a multi-stage one, it consists in seven steps, namely: protection of the primary amino group of tryptamine by benzoyl chloride, reduction of the position of the 2-indol cycle by phenylborane in an atmosphere of argon for 27.5 hours, bromination of the resulting product with bromine in the presence of a copper catalyst, treatment of the thus-obtained bromoderivative with sodium methylate and then with an alkali, followed by preparation of serotonin by way of a catalytical hydrogenation of the resulting 5-hydroxymethyltryptamine.

This method is of a multi-stage character and features a rather complicated procedure involving repeated extractions, crystallizations, lasting heatings within the predetermined temperature ranges and the use of toxic reagents.

It is also known to prepare 3,4-dihydroxyphenylalanine from tyrosine by way of a multi-stage synthesis, wherein the starting product is successively subjected to nitration with a fuming nitric acid, reduction with zinc and hydrochloric acid, followed by diazotization with sodium nitrite at a lowered temperature with an obligatory simultaneous protection of the aliphatic amino group and in the final stage the product is subjected to hydrolyzation with an alkali (cf. Zeitschrift für physiologisches Chemie, 1933, No. 219, 233S; Helv. Chim. Acta, 1921, No. 4, 657–659S).

The above-described method is also of a multi-stage character, it features a complicated procedure and a low yield of the final product not exceeding 15–20% as calculated for the starting product.

BRIEF DESCRIPTION OF THE INVENTION

Known is a method for preparing 3-hydroxyphthalic acid from phthalic acid by way of nitration, reduction, diazotization and hydrolysis. This method also features a low yield of the final product not exceeding 25%.

It is the main object of the present invention to increase the desired product yield.

It is another object of the present invention to simplify the production process.

These objects are accomplished by providing a method for preparing hydroxy compounds of the aromatic and heteroaromatic series according to the present invention, having the following general formula:

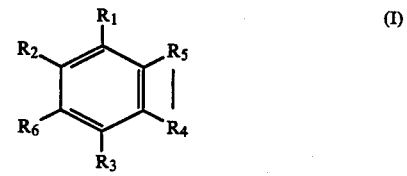

wherein when $R_1 = -COOH$, $-CH_2CH(NH_2)COOH$, then $R_2 = -OH$, $-H$, $-COOH$, $R_3 = -H$, $-OH$; $R_4$ and $R_5 = -H$; $R_6 = -OH$; and when $R_1$; $R_6$; $R_3 = -H$, then $R_2 = -OH$; $R_4 = >NH$, $R_5 = -CR_7 = CHR_4$, wherein $R_7$ is $-CH_2CH_2NH_2$ or $-CH_2-CH(NH_2)COOH$, according to the present invention an aromatic or a heteroaromatic compound of the general formula:

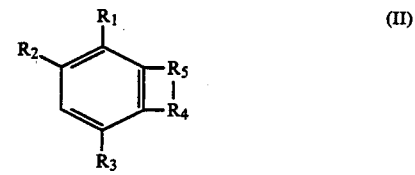

wherein when $R_1 = -COOH$, $-CH_2CH(NH_2)COOH$, then $R_2 = -OH$, $-H$, $-COOH$; $R_3 = -H$, $-OH$; $R_4$ and $R_5 = -H$; and when $R_1$, $R_2$, $R_3 = -H$, then $R_4 = NH$; $R_5 = -CR_7 = CHR_4$, where $R_7$ is $-CH_2-CH_2-NH_2$, $-CH_2CH(NH_2)COOH$ is subjected to hydroxylation in the presence of oxygen, phenazine catalysts of the general formula:

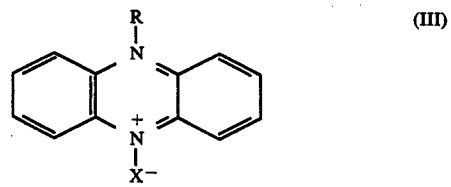

wherein R is $-CH_3$, $C_2H_5$,

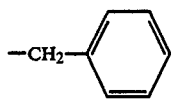

styrene-divinylbenzene copolymer; $X^-$ is $CH_3SO_4^-$, $C_2H_5SO_4^-$, $Cl^-$, and a reducing agent performing a one-electron reduction of the heterocyclic nitrogen of the phenazinium cycle at a pH of the reaction medium ranging from 2.0 to 5.5, followed by isolation of the desired product.

To increase the desired product yield, it is advisable to use, as the reducing agent, cellulose modified with 1,4-dihydronicotinamide, or hydrazine and Raney nickel, or a cathode with a potential ensuring one-electron reduction of the heterocyclic nitrogen of the phenazinium cycle.

For obtaining 2,3-dioxybenzoic acid as a phenazine catalyst, it is preferable to use methylsulphate of N-methylphenazinium and to carry out the process in the presence of a reducing agent of cellulose modified with 1,4-dihydronicotinamide at a pH ranging from 4.5 to 5.5 or in the presence of a reducing agent, namely, hydrazine hydrate and Raney nickel at a pH of 2.0 to 5.5. For obtaining 3,4-dioxyphenylalanine as a phenazine catalyst, it is preferable to use methylsulphate of N-methylphenazinium and to carry out the process in the presence of a reducing agent, namely hydrazine hydrate and Raney nickel at a pH of 3.0 to 5.5 or in the presence of a cathode with a potential of −0.3 to −0.5 V with respect to a calomel electrode.

DETAILED DESCRIPTION OF THE INVENTION

The process is carried out as follows.

The starting aromatic and heteroaromatic compounds of the general formula (II) are dissolved in an acid buffer solution at a pH within the range of from 2.0 to 5.5 and mixed with a phenazine catalyst of the general formula (III) and a reducing agent performing a one-electron reduction of the heterocyclic nitrogen of the phenazinium cycle. Oxygen (air oxygen) or hydrogen peroxide or a mixture of both is admitted into the resulting mixture. Cellulose modified with 1,4-dihydronicotinamide, or hydrazine hydrate and Raney nickel is used as the reducing agent. Furthermore, the one-electron reduction of the heterocyclic nitrogen of the phenazinium cycle is carried out on the cathode.

The process proceeds according to the following scheme:

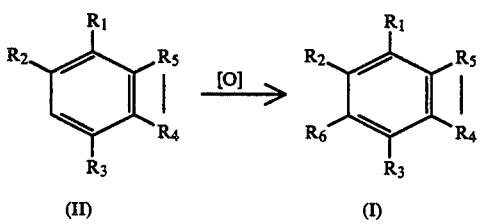

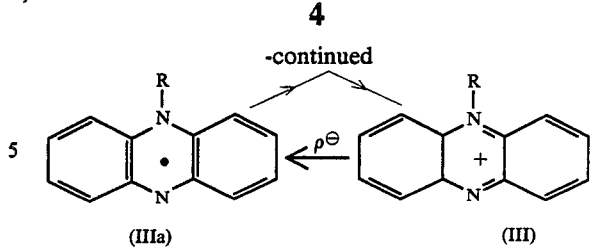

According to the above scheme, at first three occurs the one-electron reduction of the heterocyclic nitrogen of the phenazinium catalyst (III) to give a free-radical form (IIIa) which is stabilized by the acidic medium. The free-radical form—catalyst (IIIa) reacts with the starting product (II) and oxygen thus forming an oxygenating complex which, upon decomposition thereof, gives the desired product (I) and the initial form of the catalyst (III).

The recovery of the desired product is carried out by following a conventional procedure. The desired product yield is as high as 95%.

The method according to the present invention makes it possible to substantially simplify the production process rendering it a single-stage one, to eliminate the use of toxic reactants and increase the desired product yield up to 95% (instead of 25% in the prior art methods).

For a better understanding of the present invention, some specific examples are given hereinbelow by way of illustration.

EXAMPLE 1

17 l of a 0.006M solution of citric acid are poured into a reactor and pH is brought to 4.5 by means of caustic potash, whereafter 17 g of cellulose modified with 1,4-dihydronicotinamide with the content of 0.2 mmol/g of dihydronicotinamide groups and 0.03 g of 9-methylphenazinium methylsulphate are added thereto and allowed to stand for 3 hours. Then 1.1 g of salicylic acid is added and the mixture is vigorously stirred for additional 3 hours. Cellulose modified 1,4-dihydronicotinamide is filtered off, the solution is evaporated to 100 ml and extracted with chloroform. The resulting extract is evaporated to 50 ml and cooled. The formed precipitate is crystallized with a mixture consisting of water and ethanol in the ratio of 1:1 to give 0.9 g of 2,3-dihydroxybenzoic acid (82% as calculated for the starting compound) having its melting point of 203°–204° C. Composition, in %, is as follows:

Found, %: C 54.51, H 3.92. $C_7H_6O_4$, M=154.01. Calculated, %: C 54.56, H 3.89.

EXAMPLE 2

The process is conducted in a manner similar to that described in Example 1 hereinbefore, except that 1 ml of the citrate buffer, 1 mg of cellulose modified with 1,4-dihydronicotinamide and 0.03 mg of 9-methylphenazium methyl sulfate and 0.3 mg. of salicylic acid are used. As a result, 0.28 mg. of 2,3-dihydroxybenzoic acid is obtained (95% as calculated for the starting compound) having m.p. 203°–204° C. The composition, in %, is as follows:

Found, %: C 54.52, H 3.93, $C_7H_6O_4$ M=154.01. Calculated, %: C 54.56, H 3.89.

EXAMPLE 3

The process is conducted as described in Example 1, except that instead of salicylic acid 0.15 g of 4-hydroxybenzoic acid, 2.1 g of cellulose modified with 1,4-dihydronicotinamide, 2.1 l. of the citrate buffer and 0.03 g of 9-ethylphenazinium ethylsulphate are used.

0.09 g of a white crystal powder of 3,4-dihydroxybenzoic acid is obtained (62% based on the starting compound). Melting point is 172°–173° C. The composition, in %, is as follows:

Found, %: C 54.52, H 3.94; $C_7H_6O_4$ M=154.01. Calculated, %: C 54.56, H 3.89.

EXAMPLE 4

0.15 g of salicylic acid and 0.03 g of 9-methylphenazinium methylsulphate are placed into a reactor and dissolved in 100 ml of water acidified by acetic acid to the pH=3.0; then 3.0 ml of hydrazine hydrate and 0.5 g of Raney nickel are added thereto. Thereafter, the reaction mixture is maintained for 4 hours under vigorous stirring. Then nickel is filtered-off, the resulting mixture is evaporated to 10 ml and extracted with chloroform. After cooling the precipitated desired product is crystallized by a mixture of water and ethanol in the ratio of 1:1 to give 0.13 g of 2,3-dihydroxybenzoic acid (90% as calculated for the starting compound) having m.p. 203°–204° C. The composition, in %, is as follows:

Found, %: C 54.52, H 3.93; $C_7H_6O_4$; M=154.01. Calculated, %: C 54.56, H 3.89.

EXAMPLE 5

The process is carried out as described in the foregoing Example 4, except that the pH of the reaction medium is maintained at 4.0 and 0.6 g of Raney nickel is added to give 0.126 g of 2,3-dihydroxybenzoic acid (84% as calculated for the starting compound) having the same characteristics as in Example 4.

EXAMPLE 6

1.8 g of tyrosine, 0.15 g of 9-methylphenazinium methylsulphate are placed into a reactor, dissolved in 1,000 ml of water. The resulting solution is acidified with acetic acid to the reaction medium pH of 4.5 and added with 30 ml of hydrazine hydrate and 5 g of Raney nickel. After filtering-off nickel, the resulting reaction mixture is evaporated to dryness under the pressure of 20 mm Hg, the residue is dissolved in 20 ml of methanol and the mixture is chromatographically separated into alumina and the desired product by eluting with a mixture consisting of n-propanol and a 34% aqueous ammonia taken in the ratio of 70:3. 1.1 g of 3,4-dihydroxyphenylalanine is thus obtained; the yield is 61% as calculated for the starting compound, m.p. of the product is 271°–272° C. The composition, in percent, is as follows:

Found, %: C 54.80, H 5.61, N 7.08; $C_9H_{11}O_4N$; M=197.1. Calculated, %: C 54.82, H 5.58, N 7.11.

EXAMPLE 7

The process is conducted as described in the foregoing Example 6, the difference being in that the pH of the reaction medium is maintained at 5,5. 1,04 g of 3,4-dihydroxyphenylalamine is obtained (58% as calculated for the starting compound) having the same properties as described in Example 6.

EXAMPLE 8

The process is conducted as described in the foregoing Example 6, except that instead of tyrosine 0.21 g of tryptophane is used, the reaction medium pH is 4.0. 0.105 g of 5-hydroxytryptophan is obtained (50% as calculated for the starting compound) having melting point of 287°–288° C. The composition, in percent, is as follows:

Found, %: C 59.89, H 5.40, N 12.83; $C_{11}H_{12}N_2O_3$; M=200.22. Calculated, %: C 59.98, H 5.45, N 12.79.

EXAMPLE 9

1.81 g of tyrosine and 0.15 g of 9-methylphenazinium methylsulphate are placed into a reactor, the resulting mixture is dissolved in 1 liter of water, acidified with a 0.1M hydrochloric acid to the pH of 2.0 and carbon electrodes are immersed into the solution.

The potential of 0.3 V relative to a calomel electrode is set on the cathode. The predetermined voltage is maintained for 8 hours and air is bubbled at a rate of 100–150 ml/min. Then the reaction mixture is evaporated to dryness under the pressure of 20 mm Hg. The resulting residue is dissolved in 20 ml of methanol and chromatographically separated into alumina and the desired product by elution with a mixture consisting of n-propanol and a 34% aqueous ammonia in the ratio of 70:3.

1.1 g (61% as calculated for the starting compound) of 3,4-dihydroxyphenylalanine with the m.p. of 271°–272° C. is obtained. The composition, in percent, is as follows:

Found, %: C 54.83, H 5.64, N 7.01; $C_6H_{11}O_4N$, M=197.1. Calculated, %: C 54.80, H 5.88, N 7.11.

EXAMPLE 10

The process is carried out in a manner similar to that described in the foregoing Example 9, except that the reaction medium pH is 3.5 and the process duration is 7 hours. 1.26 g (65% as calculated for the starting compound) of 3,4-dihydroxyphenylalanine having the same characteristics as in Example 9 is obtained.

EXAMPLE 11

The process is conducted as in Example 9 hereinabove, except that instead of tyrosine 0.16 g of tryptamine and 0.03 g of 9-methylphenazinium methylsulphate are used and 0.226 g of creatinine is added to the solution. The reaction medium is acidified with a 0.1M sulphuric acid and the potential of 0.5 V is set relative to a saturated calomel electrode.

After 12 hours of the reaction, the resulting mixture is evaporated to the volume of 100 ml and added with 500 ml of acetone. The residue is filtered off, dissolved in 50 ml of water and reprecipitated using 200 ml of acetone to give 0.24 g (61% as calculated for the starting compound) of servotonin creatinine sulphate in the form of white crystals having melting point of 208°–206° C.

Paper chromatography in the system butanol-acetic acid-water in the volume ratio of 4:1:1 respectively gives the $R_f$=0.33 which is consistent with the $R_f$ of a commercial sample of serotonin creatine sulphate available from the "FERAK" company.

EXAMPLE 12

The process is conducted as in Example 9 hereinbefore, except that 10 ml of a 0.1M solution of $H_2O_2$ are added and the process duration is 16 hours. 0.17 g of serotonin creatinine sulphate (43% as calculated for the starting product) having m.p. of 208°–209° C. is obtained.

EXAMPLE 13

0.15 g of 9-methylphenazinium methylsulphate and 1.64 g of phthalic acid are placed into a reactor, the reaction medium is acidified with hydrochloric acid to the pH of 4.5 and the cathode potential is kept within the range of 10.4±0.1 V relative to a saturated calomel electrode. Air is bubbled through the solution at a rate of 100–150 ml/min. The process is conducted for 5 hours and the reaction mixture is evaporated not to dryness, but to a volume of 15–20 ml and the residue is added with 20 ml of ethanol. The resulting mixture is chromatographically separated on silica gel by elution with a mixture consisting of chloroform, cyclohexane, acetic acid and ethanol in the ratio of 36:4:9:8 respectively.

1.17 g (65% as calculated for the starting product) of 3-hydroxyphthalic acid is obtained in the form of a white crystalline substance melting at 243°–244° C. The product composition, in percent, is as follows:

Found, %: C53.41, H 3.30, $C_8H_6O_5$; M=182.01. Calculated, %: C 53.33, H 3.33.

EXAMPLE 14

The process is conducted as described in Example 13 hereinabove, except that pH of the reaction medium is maintained at 2.5 and the process duration is 8 hours.

1.17 g (58% as calculated for the starting substance) of 3-hydroxyphthalic acid melting at 243°–244° C. is obtained.

EXAMPLE 15

The process is conducted as in Example 13, except that instead of 9-methylphenazinium methylsulphate 0.16 g of 9-ethylphenazinium ethylsulphate is used and the potential is set at 0.7±0.1 V relative to a saturated calomel electrode.

1.16 g (63% as calculated for the starting product) of 3-hydroxyphthalic acid having the same characteristics as in Example 13 is obtained.

EXAMPLE 16

The process is conducted as in Example 13, except that instead of air bubbling 10 ml of a 1M solution of hydrogen peroxide are added under stirring. 1.16 g (63% as calculated for the starting product) of 3-hydroxyphthalic acid having the same characteristics as in Example 11 hereinbefore is obtained.

EXAMPLE 17

The process is conducted as in Example 13, except that instead of air bubbling 10 ml of a 1M solution of hydrogen peroxide are added under stirring to give 1.07 g (58% as calculated for the starting product) of 3-hydroxyphthalic acid having the same characteristics as in Example 11.

EXAMPLE 18

0.24 g of tryptamine and 0.06 g of 9-ethylphenazinium ethylsulphate are placed into a reactor and dissolved in 1,000 ml of water, the reaction medium is acidified with a 0.1M solution of sulphuric acid to the pH of 3.0 and 0.342 g of creatinine is added thereto. Platinum electrodes are immersed into the solution and the potential of 0.6 V is set on the cathode relative to a saturated calomel electrode. Air is bubbled through the solution for 15 hours at a rate of 3–5 ml/min. Thereafter the solution is evaporated to the volume of 100 ml under the pressure of 20 mm Hg and 500 ml of acetone are added thereto. The precipitate is filtered off, dissolved in 50 ml of water and reprecipitated with 200 ml of acetone to give 0.24 g (61% as calculated for the starting compound) of serotonin creatine sulphate in the form of white crystals melting at 208°–209° C.

EXAMPLE 19

The process is conducted in a manner similar to that described in Example 18, except that the pH of the reaction medium is maintained at 2.5 and the process duration is 18 hours. 0.33 g (56% as calculated for the starting product) of serotonin creatinine sulphate melting at 208°–209° C. is thus obtained.

EXAMPLE 20

0.21 g of tryptophan and 0.03 g of 9-methylphenazinium methylsulphate are placed into a reactor and dissolved in 1,000 ml of water. The reaction medium is acidified with a 0.1M hydrochloric acid to the pH of 4.5 and carbon electrodes are placed into the solution; the potential of 0.5 V is set on the cathode relative to a saturated calomel electrode. Air is bubbled for 6 hours at a rate of 100–150 ml/min. Then the solution is evaporated to dryness under the pressure of 20 mm Hg. Thereafter the residue is dissolved in 20 ml of methanol and chromatographically separated into alumina and the desired product by elution with a mixture consisting of n-propanol and a 34% aqueous ammonia taken in the volume ratio of 70:3.

The fraction giving a green colour with $FeCl_3$ is evaporated to give 0.14 g (65% as calculated for the starting product) of 5-hydroxytryptophan melting at 287°–288° C. is obtained. The product has the following composition, in percent:

Found, %: C 59.89, H 5.40, N 12.83, $C_{11}H_{12}N_2O_3$, M=220.22. Calculated, %: C 59.98, H 5.45, N 12.7.

EXAMPLE 21

25 g of a macroporous styrene-divinylbenzene copolymer with the content of nitrogen of 3.65% modified with phenazinium through the methylene bridge are charged into a reactor and suspended in 100 ml of distilled water for 24 hours. Then the resulting suspension is washed with a diluted hydrochloric acid (pH=3) and placed into a vessel with platinum electrodes. 100 ml of a diluted HCl (pH=3) are added thereto and the potential of 0.65 V relative to a saturated calomel electrode is set on the cathode. Then the acidic solution is drained and 100 ml of a solution containing 0.21 g of tryptophane and 10 ml of a 1M solution of $H_2O_2$ is added to the reaction mixture and the voltage is maintained at the set value for 12 hours. Then the solution is drained, the suspension is washed with a 0.01M solution of HCl. Both solutions are combined, neutralized with sodium carbonate to the pH of 4.5, evaporated under the pressure of 20 mm Hg to dryness. The resulting residue is dissolved in 20 ml of methanol and chromatographically separated into alumina and the desired product by elution with a mixture consisting of n-propanol and a 34% aqueous ammonia in the volume ratio of 70:3.

The fraction of 5-hydroxytryptophan is determined by green colour with $FeCl_3$.0.165 g (75% as calculated for the starting product) of 5-hydroxytryptophan melting at 271°-272° C. is thus obtained. The product has the following composition, in percent:

Found, %: C 59.89, H 5.40, N 12.83, $C_{11}H_{12}N_2O_3$, M=220.22. Calculated, %: C 59.98, H 5.45, N 12.72.

EXAMPLE 22

The process is conducted following the procedure described in the foregoing Example 21, except that instead of tryptophan 0.15 g of p-hydroxybenzoic acid is used and the voltage is applied for 10 hours. 0.12 g (75% as calculated for the starting compound) of 3,4-dihydroxybenzoic acid is obtained; the product melting point is 172°-173° C.

EXAMPLE 23

The process is conducted as described in Example 21, except that instead of tryptophan 0.16 g of phthalic acid is used and the potential on the cathode is maintained equal to 0.6 V relative to a saturated calomel electrode for 8 hours; pH of the reaction medium is 2.5. After evaporation of the suspension to dryness 20 ml of ethanol are added thereto and the mass is chromatographically separated on silica gel by elution with a mixture consisting of chloroform, cyclohexane, acetic acid and ethanol in the volume ratio of 36:4:9:8 respectively. The fraction giving a red colour with $FeCl_3$ is evaporated and recrystallized from water to give 0.1 g (63% as calculated for the starting product) of 3-hydroxyphthalic acid in the form of a white cyrstalline substance melting at 143°-144° C.

EXAMPLE 24

The procedure of Example 21 is repeated, except that instead of tryptophan 0.15 g of salicylic acid is used, the pH is equal to 3.5 and the cathode potential is maintained equal to 0.2 V relative to a saturated calomel electrode. Instead of adding hydrogen peroxide, air is bubbled at a rate of 150-200 ml/min for 14 hours. After evaporation the residue is dissolved in ethanol and separated chromatographically to give 0.08 g (50% as calculated for the starting product) of 2,3-dihydroxybenzoic acid melting at 203°-204° C.

What we claim is:

1. A method for preparing hydroxy compounds of the aromatic and heteroaromatic series of the general formula:

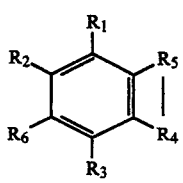

wherein when $R_1$=—COOH/or —$CH_2CH(NH_2)$COOH; then $R_2$=—OH, —H, —COOH; $R_3$=—H, or —OH; if $R_2$=—OH, —COOH, $R_4$, $R_5$=—H; $R_6$=—OH and when $R_1$, $R_6$, $R_3$=—H, then $R_2$=—OH; $R_4$=½NH; $R_5$=—$CR_7$=$CHR_4$, where $R_7$=—$CH_2$—$CH_2$—$NH_2$, —$CH_2$—$CH(NH_2)$COOH, consisting essentially of hydroxylation of aromatic and heteroaromatic compounds of the general formula:

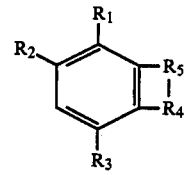

wherein when $R_1$=—COOH, —$CH_2$/or $CH(NH_2)$COOH, then $R_2$=—OH, —H/or —COOH; $R_3$=—H/or —OH; if $R_2$=—OH, —COOH, $R_4$, $R_5$=—H; and when $R_1$, $R_2$, $R_3$=—H, then $R_4$=½NH; $R_5$=—$CR_7$=$CHR_4$, where $R_7$ is —$CH_2$—$CH_2$—$NH_2$, —$CH_2$—$CH(NH_2)$COOH, in the presence of oxygen, a phenazine radical-oxygen complex of the general formula:

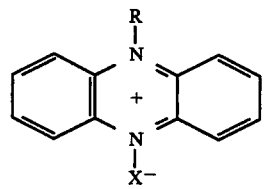

wherein R is

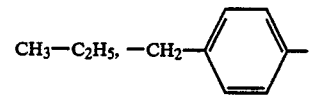

Styrene-benzene-divinyl copolymer;
$X^-$=$CH_3SO_4$, $C_2H_5SO_4$, $Cl^-$, and which was obtained by performing a one-electron reduction of the heterocyclic nitrogen of the phenazinium cycle, at a pH of the reaction medium ranging from 2.0 to 5.5 by reaction with oxygen, followed by isolation of the desired product.

2. A method according to claim 1, wherein the reducing agent is selected from the group consisting of cellulose modified with 1,4-dihydronicotinamide, hydrazine hydrate and Raney nickel or a cathode with a potential ensuring carrying out of one-electron reduction of heterocyclic nitrogen of the phenazinium cycle.

3. A method according to claim 1, for preparing 2,3-dihydroxy-benzoic acid wherein N-methylphenazinium methylsulphate is the phenazine catalyst and the process is carried out in the presence of cellulose modified with 1,4-dihydronicotinamide at a pH of 4.5 to 5.5.

4. A method according to claim 1, for preparing 2,3-dihydroxy-benzoic acid wherein N-methylphenazinium methylsulphate is the phenazine catalyst and the process is carried out in the presence of hydrazine hydrate and Raney nickel as the reducing agent at a pH of 2.0 to 5.5.

5. A method according to claim 1, for preparing 3,4-dihydroxyphenylanine, wherein N-methylphenazinium methylsulphate is the phenazinium catalyst and the process is carried out in the presence of hydrazine hydrate and Raney nickel as the reducing agent at a pH of 3.0 to 5.5.

6. A method according to claim 1, for preparing 3,4-dihydroxyphenylalanine, wherein N-methylphenazinium methylsulphate is the phenazinium catalyst and the process is carried out in the presence of a cathode with a potential of −0.3 V to −0.5 V with respect to a calomel electrode.

* * * * *